United States Patent [19]

Razin et al.

[11] Patent Number: 5,296,371

[45] Date of Patent: Mar. 22, 1994

[54] DNA ENCODING SPIROPLASMA SP. DNA METHYLASE

[75] Inventors: Aharon Razin; Shlomo Rottem; Pinhas F. Renbaum, all of Jerusalem, Israel

[73] Assignee: Yissum Research Development Company of the Hebrew University of Jerusalem, an Israeli Corp.

[21] Appl. No.: 771,525

[22] Filed: Oct. 4, 1991

Related U.S. Application Data

[63] Continuation of Ser. No. 390,649, Aug. 7, 1989, abandoned.

[51] Int. Cl.$^5$ .................... C12N 1/21; C12N 1/15; C12N 15/70; C12N 15/54
[52] U.S. Cl. .................... 435/252.3; 435/252.33; 435/254.11; 435/320.1; 435/172.3; 435/193; 536/23.7
[58] Field of Search .................... 435/91, 193, 172.3, 435/320.1, 252.33, 252.3; 536/27, 23.7

[56] References Cited

U.S. PATENT DOCUMENTS 4,886,750  12/1989  Bertola et al. .................... 435/822

FOREIGN PATENT DOCUMENTS 0321268  6/1989  European Pat. Off. ............ 435/193
0321270  6/1989  European Pat. Off. ............ 435/193

OTHER PUBLICATIONS

Caserta et al. (1987) "Cloning, Sequencing of HhaI Methyltransferase", JBC, vol. 262 (10), pp. 4770–4777.
Kiss et al., (1985) "Nucleotide Sequence of BsuRI", NAR, vol. 13, pp. 6403–6421.
Som et al. (1987) "Nucleotide Sequence +expression of EcoRII", NAR, vol. 15, pp. 313–332.
Sznyter et al. (1987) "Nucleotide sequence and characterization of methylase protein", NAR, vol. 15, pp. 8249–8266.
Wilson, Gene 74:281–289 (1988).
Razin, A., Cedar, H., and Riggs, A. D., eds in DNA Methylation Biochemistry and Biological Significance, Springer-Verlag (1984) pp. 1–10.
Bestor, T., et al. J. Mol. Biol. 203, 971–983 (1988).
Razin, A., et al., Biochem. Biophys. Acta 782, 331–342 (1984).
Nur, I., et al., J. Bacteriol 164, 19–24 (1984).
Saglio, et al., Physiol. Veg. 9, 569 (1971).
Marmur, J., J. Mol. Biol. 3, 208 (1961).
Raleigh, et al., Nucleic Acids Res. 16, 1563 (1988).
Studier, F. W., et al. J. Mol. Biol. 189, 113–130 (1986).
Kunkel, T. A., Proc. Natl. Acad. Sci. USA 82, 488 (1985).
Hanahan, D., DNA Cloning, vol. 1, D. M. Glover, ed., JRL Press (Oxford 1986) pp. 109–135.
Gruenbaum, Y., et al. FEBS Lett. 124, 67–71 (1981).
Walder et al. (1983) "Cloning of the MspI Modification Enzyme", JBC, vol. 258, pp. 1235–1241.

*Primary Examiner*—Richard A. Schwartz
*Assistant Examiner*—Nancy T. Vogel
*Attorney, Agent, or Firm*—David G. Conlin; Gregory D. Williams; David S. Resnick

[57] ABSTRACT

The present invention is directed to a method for cloning and producing the Spiroplasma sp. strain MQ1 DNA methylase by (1) introducing the Spiroplasma methylase gene into a host whereby the methylase gene is expressed; (2) fermenting the host which contains the vector encoding and expressing the Spiroplasma methylase and (3) purifying the Spiroplasma methylase from the fermented host which contains the vector encoding and expressing the Spiroplasma DNA methylase activity.

5 Claims, 6 Drawing Sheets

```
1     GATCTTGATAATTCAACTTTATTTGGATGTTGTGAAATGTAGATAAATCTTACATTTTTT

61    ATTGTAAAATCTTATTAGATTGTTTTTTTAGAGGAGCTAAAAATGAGCAAAGTAGAAAAT
                                                  M  S  L  V  E  N    6

121   AAAACAAAAAAACTTAGAGTATTTGAAGCTTTTGCTGGAATTGGTGCTCAAAGAAAAGCC
      K  T  K  K  L  R  V  F  E  A  F  A  G  I  G  A  Q  R  K  A    26

181   TTGGAGAAAGTCAGAAAAGATGAATATGAAATAGTAGGGCTTGCTGAATGATATGTTCCT
      L  E  K  V  R  K  D  E  Y  E  I  V  G  L  A  E  W  Y  V  P    46

241   GCAATTGTTATGTATCAAGCTATACACAACAATTTTCATACAAAGTTGGAGTATAAATCA
      A  I  V  M  Y  Q  A  I  H  N  N  F  H  T  K  L  E  Y  K  S    66

301   GTTTCTAGAGAAGAAATGATTGACTATTTGGAAAATAAAACACTATCTTGAAACTCAAAA
      V  S  R  E  E  M  I  D  Y  L  E  N  K  T  L  S  W  N  S  K    86

361   AATCCAGTATCTAATGGTTATTGGAAGAGAAAAAAAGATGATGAACTTAAAATTATATAT
      N  P  V  S  N  G  Y  W  K  R  K  K  D  D  E  L  K  I  I  Y    106

421   AATGCAATTAAGTTATCTGAAAAAGAGGGTAATATTTTTGATATTAGAGACCTTTACAAA
      N  A  I  K  L  S  E  K  E  G  N  I  F  D  I  R  D  L  Y  K    126

481   AGAACTTTGAAAAATATAGATTTATTAACATATTCATTTCCTTGTCAAGACTTATCTCAA
      R  T  L  K  N  I  D  L  L  T  Y  S  F  P  C  Q  D  L  S  Q    146

541   CAGGGTATTCAAAAGGGTATGAAAAGAGGTTCTGGTACTAGATCAGGTCTCTTATGAGAA
      Q  G  I  Q  K  G  M  K  R  G  S  G  T  R  S  G  L  L  W  E    166

601   ATTGAAAGAGCTTTGGATTCAACTGAAAAAAATGACTTACCAAAATACTTGTTAATGGAA
      I  E  R  A  L  D  S  T  E  K  N  D  L  P  K  Y  L  L  M  E    186

661   AATGTAGGAGCTCTTCTTCACAAGAAGAATGAAGAAGAACTAAATCAATGAAAGCAAAAA
      N  V  G  A  L  L  H  K  K  N  E  E  L  N  Q  W  K  Q  K       206

721   TTAGAAAGTCTTGGCTATCAAAACTCAATTGAAGTTTTGAATGCCGCTGACTTCGGTTCC
      L  E  S  L  G  Y  Q  N  S  I  E  V  L  N  A  A  D  F  G  S    226

781   TCACAAGCAAGAAGAAGAGTTTTTATGATATCTACTTTAAATGAATTTGTTGAACTACCA
      S  Q  A  R  R  R  V  F  M  I  S  T  L  N  E  F  V  E  L  P    246

841   AAGGGAGATAAAAAACCTAAAAGTATCAAAAAAGTTTTAAATAAAATAGTTTCTGAAAAA
      K  G  D  K  K  P  K  S  I  K  K  V  L  N  K  I  V  S  E  K    266

901   GATATTTTAAATAATTTATTGAAATATAATTTAACTGAATTTAAAAAAACAAAATCAAAT
      D  I  L  N  N  L  L  K  Y  N  L  T  E  F  K  K  T  K  S  N    286

961   ATAAATAAAGCTTCACTGATTGGTTACAGTAAATTTAATTCAGAAGGTTATGTTTATGAT
      I  N  K  A  S  L  I  G  Y  S  K  F  N  S  E  G  Y  V  Y  D    306

1021  CCTGAATTTACAGGACCAACCTTAACTGCAAGCGGTGCAAATTCAAGAATAAAAATCAAA
      P  E  F  T  G  P  T  L  T  A  S  G  A  N  S  R  I  K  I  K    326

1081  GATGGATCTAATATTAGAAAAATGAATTCAGACGAAACTTTCTTATATATTGGGTTTGAT
      D  G  S  N  I  R  K  M  N  S  D  E  T  F  L  Y  I  G  F  D    346

1141  TCACAAGATGGAAAAAGAGTAAATGAAATTGAATTTTTAACTGAAAATCAAAAAATATTT
      S  Q  D  G  K  R  V  N  E  I  E  F  L  S  E  N  Q  K  I  F    366
```

FIG. 5-1

1201 GTTTGTGGAAATTCAATATCAGTAGAAGTTTTGGAAGCGATTATAGATAAAATTGGAGGT
      V  C  G  N  S  I  S  V  E  V  L  E  A  I  I  D  K  I  G  G   386

1261 TAATACATGTCAATAAAAGATAAAACATATTTAGTAAATGTTCCTATAATAAGAAAAAAT

1321 TTTTTTTCTACTAATTCAGCTAAGTTTAAGGGAAATTTGCAAATTATTTCAAATGATTTT

1381 GGAATAATAAAAGATTGAAAAATTGAATTCAAAGAAGTTTGAATAGATATATTTACAACC

1441 CCAAGGTGATTTAGTGATAAGCCTAGCTTATTTAAATATAGGGAAAGGCTTTTTGAAGAA

1501 TTAAATTTAATTCAGGAGCACAGACCTTCAAAAAGATC 1538

FIG. 5-2

DNA ENCODING SPIROPLASMA SP. DNA METHYLASE

This is a continuation of copending application Ser. No. 07/390,649 filed on Aug. 7, 1989, now abandoned.

BACKGROUND OF THE INVENTION

The present invention relates to recombinant DNA which encodes a DNA methylase which methylates cytosine residues which are 5' neighbors of guanine. More specifically, it relates to recombinant DNA which encodes the DNA methylase, M.Sss MQ1, obtainable from the Spiroplasma sp. strain MQ1 and to the production of this enzyme from the recombinant DNA.

DNA methylases transfer methyl groups from the universal methyl donor S-adenosyl methionine to specific sites on the DNA. Several biological functions have been attributed to the methylated bases in DNA. The most established biological function is the protection of the DNA from digestion by cognate restriction enzymes. The restriction modification phenomenon has, so far, been observed only in bacteria. Mammalian cells, however, possess a different methylase that methylates exclusively cytosine residues on the DNA, that are 5' neighbors of guanine (CpG). This methylation has been shown, by several lines of evidence to play a role in gene activity, cell differentiation, tumorigenesis, X-chromosome inactivation, genomic imprinting and other major biological processes. (Razin, A., Cedar, H., and Riggs, R. D. eds. in DNA Methylation Biochemistry and Biological Significance, Springer-Verlag, New York, 1984).

Attempts to clone the mouse DNA methylase resulted in the cloning of full size cDNA of the mouse gene (Bestor, et. al. J. Mol. Biol. 203. 971, 1988). However, there is no evidence that strains containing the cloned gene produce the active enzyme. It should be noted also that the mammalian methylase is a "maintenance" rather than a "de novo" methylase, methylating 10–100 fold more efficiently DNA that is methylated on one of its strands as compared with unmethylated DNA (Razin and Szyf, Biochim Biophys Acta 782, 331, 1984), and is therefore, inefficient in methylating non-methylated DNA (de novo methylation) in vitro. In light of all the above a "de novo" methylating enzyme that methylates exclusively CpG sequences is in demand. Strains of bacteria that would simplify the task of purification as well as providing the means for production of the enzyme in commercial amounts would be useful.

One such methylase, the M.Sss MQ1 DNA methylase methylates exclusively CpG sequences in the DNA (Nur et al, J. Bacteriol 164, 19, 1985) thus mimicing mammalian DNA methylases. One common use of a methylase is to methylate isolated genes. This methylation renders the gene biologically inactive. Currently available methylases methylate only subsets of CpG sequences. For example, M. HpaII methylates the inner cytosine residue of the sequence CCGG, and M. HhaI methylase methylates the inner cytosine residue of GCGC. In contrast, M.Sss MQ1 methylates all CpGs in non-methylated DNA (de novo methylation).

The Spiroplasma sp. strain MQ1 is a member of the Spiroplasmatacea family which belongs to the class Mollicutes of wall-less bacteria. This bacterium is a plant parasite which grow very slowly in culture and reaches a very low cell density (at confluency $10^8$ cells/ml). Also the culture medium is relatively complex and expensive. There is, therefore, a commercial incentive to obtain strains of bacteria through recombinant DNA techniques that synthesize this methylase in abundance.

SUMMARY OF THE INVENTION

In accordance with the present invention, there is provided a recombinant DNA encoding the gene for the M.Sss MQ1 DNA methylase obtainable from Spiroplasma sp strain MQ1 (ATCC 33825), as well as to the recombinant methylase and related methods for production of the enzyme. More specifically, the invention relates to a transformed host which expresses the methylase, and to a recombinant methylase that methylates exclusively and completely CpG sequences in DNA. The M.Sss MQ1 methylase produced in accordance with the present invention is active in de novo methylation.

The preferred method for cloning this enzyme M.Sss MQl DNA methylase comprises forming a sufficient number of libraries containing DNA from Spiroplasma sp. strain MQ1, selecting for clones that express the methylase gene by incubating the library DNA with an appropriate restriction endonuclease such as, Hha I, i.e. an enzyme that cleaves its recognition sequence when it is not methylated at CG; and retransforming a host with recombinant DNA which has not been cleaved by being incubated with the restriction endonuclease and screening the resulting transformants for positive clones among survivors.

BRIEF DESCRIPTION OF THE DRAWINGS

FIG. 5 lists DNA sequence of the smallest fragment (1.5 kb) of Spiroplasma DNA that confers DNA methylase activity in the appropriate host.

DETAILED DESCRIPTION OF THE INVENTION

The present invention relates to recombinant DNA, or derivatives thereof, which encodes Spiroplasma DNA methylase or a portion thereof, as well as to the methylase produced from such a recombinant DNA. Derivatives of the recombinant DNA of the present invention include DNA sequences which reflect the degeneracy of the genetic code, substitution of one or more codons for efficient expression in microbial hosts such as E. coli, and DNA sequences which code for a biologically active portion of the methylase. The methylase gene is preferably cloned by a method which takes advantage of the fact that DNA in recombinant clones in which the gene is expressed is resistant to digestion, in vitro, by restriction endonucleases that are sensitive to 5 methyl cytosine in this recognition site. Such restriction endonucleases include Hpa II, FnuDII, HinPI, SmaI, NarI, and SalI. This resistance to digestion affords a means for selectively isolating recombinant clones which encode the M.Sss MQ1 methylase which methylates all CpG sequences.

Figure 1:
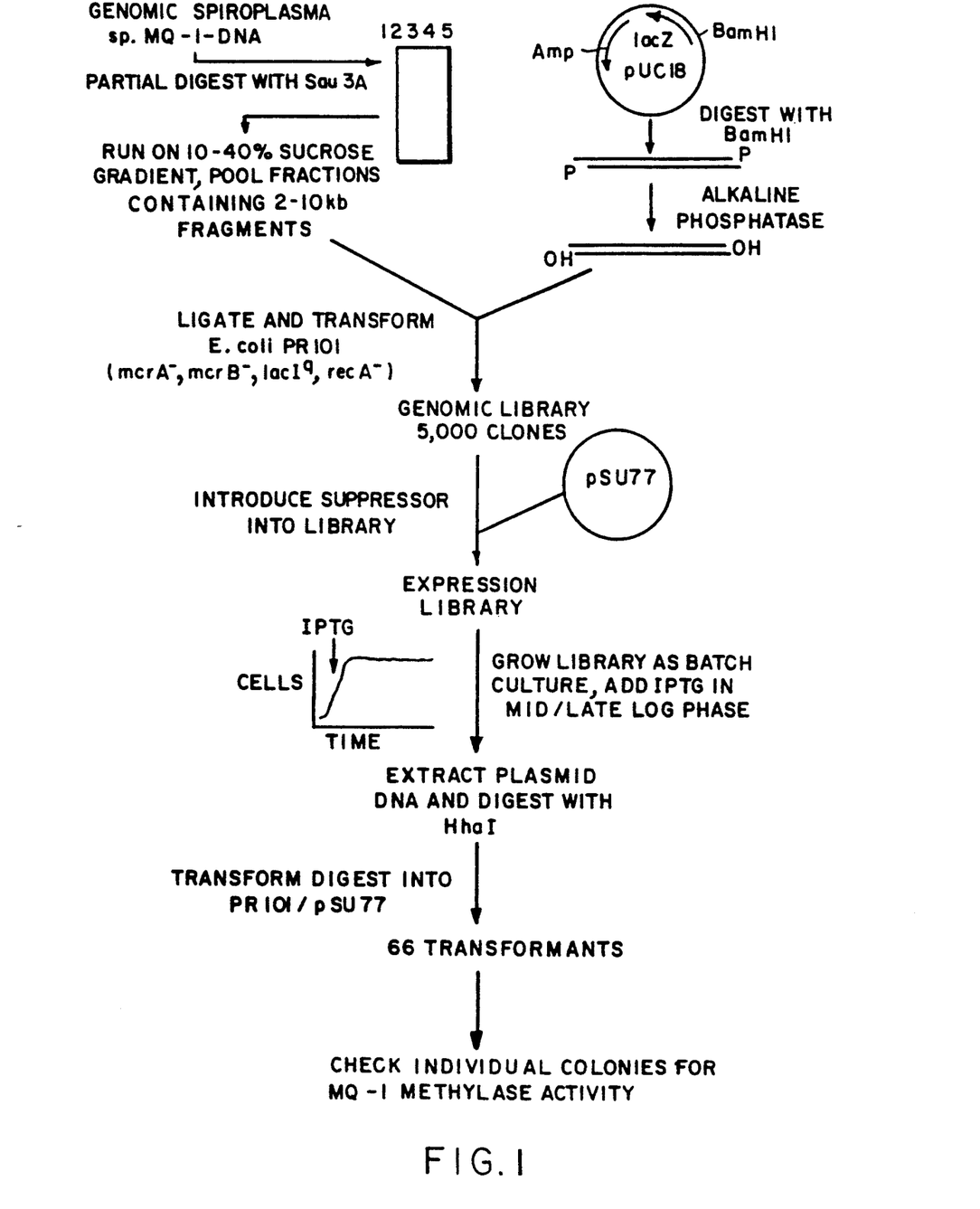
FIG. 1 illustrates the scheme for cloning the Spiroplasma sp. strain MQ1 DNA methylase gene.

The method described herein by which the DNA encoding the Spiroplasma methylase is preferably cloned and expressed is illustrated in FIG. 1, and includes the following steps:

1. The DNA is obtainable from Spiroplasma sp. strain MQ1 (ATCC 33825), which is grown to confluency in Saglio medium (Saglio et. al., Physiol. Veg. 9, 569, 1971) at 32° C. The DNA is preferably purified by the procedure described in Marmur, J., J. Mol. Biol., 3, 208, 1961, the disclosure of which is hereby incorporated by reference.

2. The DNA is partially digested with a restriction endonuclease such as Sau3AI and 3-10 kb long fragments are pooled from a 10-40% sucrose gradient.

3. The fragments are ligated to a cloning vector such as pUC18 that contains one or more HhaI sites. The ligated DNA is transformed into an appropriate host such as *E. coli* which is preferably mcrA-, mcrB-, lacI$^q$, and recA-. One such preferred host is *E. coli* PR101 a derivative of *E. coli* ER 1451 (Raleigh, E. A. et. al., Nucleic Acids Res. 16, 1563, 1988; the disclosure of which is hereby incorporated by reference) into which a recA- mutation is introduced by P1 transduction.

4. The transformed mixture is plated onto media selective for transformed cells, such as the antibiotic ampicillin. After incubation, the transformed colonies are collected into a single culture, the cell library.

5. The recombinant plasmids are purified in toto from the cell library to make the plasmid library.

Figure 2:
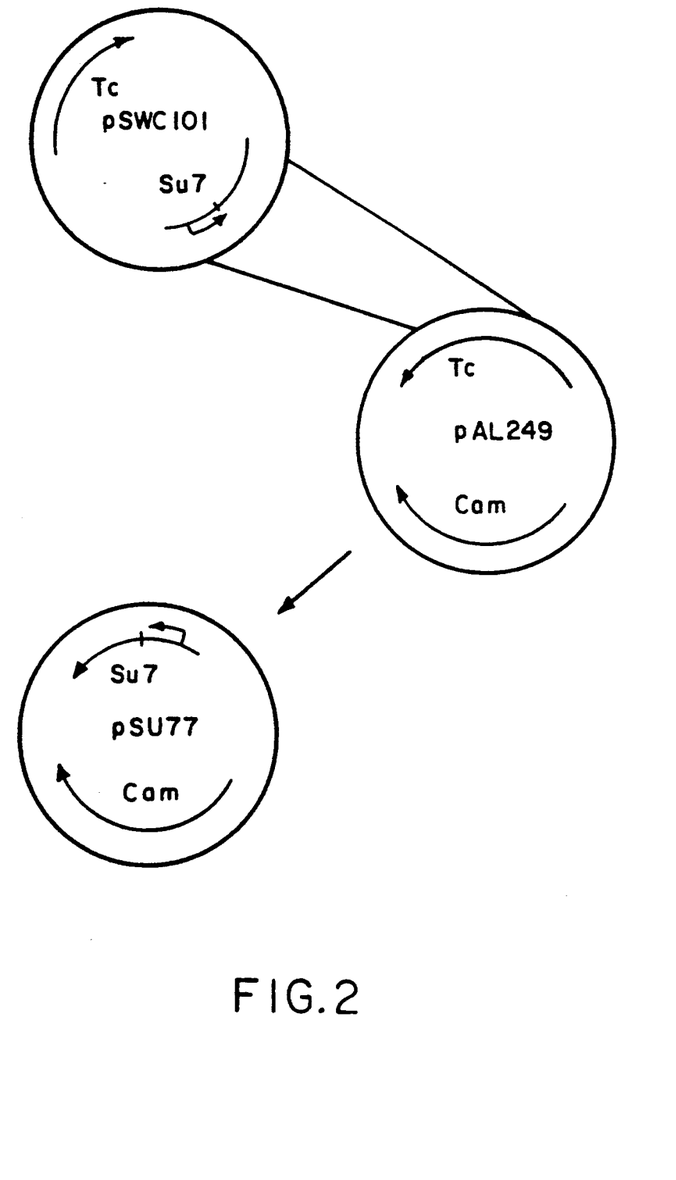
FIG. 2 describes the construction of the plasmid pSU77 harboring the opal suppressor trp T 146 including the lacUV5 promoter in the compatible vector pAL249.

6. An opal suppressor such as pSU77 is constructed by transforming the trp T suppressor from pSWC101, (see Raftery, L. A., et al., J. Bact. 158, 849, 1984, the disclosure of which is hereby incorporated by reference), into pAL249 (a derivative of pACYC 184). The construction of pSU77 is illustrated in FIG. 2. The tRNA encoded by pSU77 is used to insert the amino acid (tryptophan) at the UGA codon which occurs four times within the methylase gene. In the absence of the suppressing tRNA, UGA codons, are read as termination codons in *E. coli*, and thus interefere with the expression of biologically active methylase in *E. coli*.

7. The pSU77 plasmid or a derivative thereof is transformed into *E. coli* PR101 selecting for chloramphenicol resistant colonies.

8. PR101/pSU77 is transformed with the plasmid library and the transformants are grown in the presence of IPTG (isopropyl-β-D-thiogalactopyranoside). Ampicillin/chloramphenicol resistant colonies are collected together in LB medium.

9. The recombinant plasmid is purified and digested to completion with the HhaI restriction endonuclease. This digestion preferentially destroys unmodified, non-methylase containing clones, increasing the relative frequency of Spiroplasma sp. strain MQ1 methylase clones.

Figure 3:
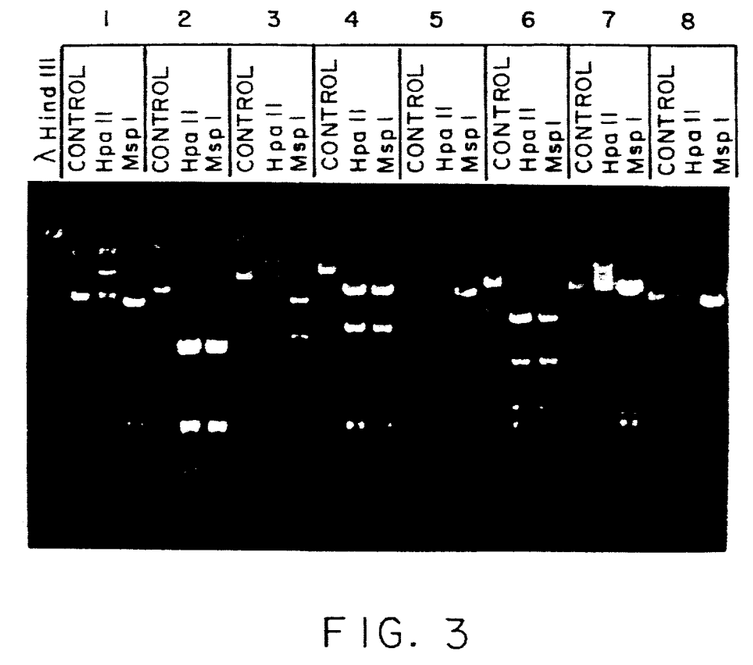
FIG. 3 demonstrates the screening for positive clones by restriction enzyme analysis using HpaII and MspI digestions.

The digested plasmid library is transformed back into an appropriate host such as PR101/pSU77, and transformants are recovered by plating onto selective media. The colonies are picked and their DNA is analyzed for the presence of the Spiroplasma methylase gene: The plasmids that carry the methylase gene are purified and incubated with the HpaII and MspI enonucleases to determine whether they are resistant to HpaII and sensitive to digestion by MspI (FIG. 3). Plasmids from clones 1, 5, 7, and 8 in FIG. 3 demonstrate resistance to cleavage by HpaII while sensitivity to cleavage by MspI. Plasmids from clones 2, 3, 4 and 6 demonstrated sensitivity to both HpaII snd MspI cleavage. Therefore clones 1, 5, 7, and 8 are likely candidates which encode an active CpG methylase. As a direct assay for CpG methylation, plasmid and cellular DNA is also purified and subjected to nearest neighbor analysis (FIG. 4) described in more detail below. The plasmids of clones that carry the Spiroplasma methylase gene should be fully modified and also chromosomal DNA should be substantially modified.

10. Clones carrying the Spiroplasma methylase are identified by preparing cell extracts of the Spiroplasma methylase clones, and assaying the extracts for Spiroplasma methylase activity as described in Example one.

11. The quantity of the Spiroplasma methylase produced by the clones may be increased by elevating the gene dosage, through the use of high copy number vectors, such as pUC19 (ATCC #37254) and by elevating the transcription rate through the use of highly active, exogenous promoters, such as T7 bacteriophage promoters (Studier, F. W., and Moffatt, B. A., J. Mol. Biol. 189, 113, 1986 the disclosure of which is hereby incorporated by reference) and by replacing the opal codons which occur within the methylase gene in DNA as TGA with TGG with site directed mutagensis as described by Kunkel, T. A., Proc. Natl. Acad. Sci. 82. 488, 1985 the disclosure of which is hereby incorporated by reference.

12. The Spiroplasma methylase may be produced from clones carrying the Spiroplasma methylase gene by propagation in a fermentor in a rich medium containing ampicillin and chloramphenicol. The cells are collected by centrifugation and disrupted by sonication or other procedures such as grinding with alumina to produce a crude cell extract containing the Spiroplasma methylase activity.

13. Recombinant methylase is preferably purified by standard protein purification techniques using affinity-chromatography such as heparin sepharose and ion-exchange chromatography. Preferably the methylase is purified by these techniques to at least about 80% homogeneity and more preferably to about 90% homogeneity. Methylases having a purity greater than about 80% are considered to be substantially pure.

Although the above outlined steps represent the preferred mode for practicing the present invention, it will be apparent to those skilled in the art that the above described approach can vary in accordance with techniques known in the art. The following example is given to illustrate embodiments of the present invention as it is presently preferred to practice. It will be understood that this example is illustrative, and that the invention is not to be considered as restricted thereto except as indicated in the appended claims.

EXAMPLE

Cloning of Spiroplasm sp. Methylase

1. DNA Purification. Spiroplasma sp. strain MQ1 cells obtainable from the ATCC (#33825) were grown to confluency and harvested by centrifugation at 4° for 10 minutes at 10,000 rpm in the Type GSA rotor of the Sorvall refrigerated centrifuge. The cells were washed twice in 0.2M NaCl, 25 mM Tris HCl pH 7.5, 5 mM EDTA and the pellet was resuspended in 10 ml of 0.1M EDTA, 1% N-lauryl sarcosine, 100 μg/ml Proteinase K and incubated for 2 hours at 50° C. RNase A (100 μg/ml was added and mixture incubated for additional 2 hours at 37° C. The treated lysate was extracted gently, twice with phenol/chloroform/isoamyl alcohol (25:24:1) and twice with chloroform/isoamyl alchol (24:1).

The aqueous phase was then dialyzed extensively against 10 mM Tris HCl pH 8, 1 mM EDTA at 4° C.

2. Digestion of DNA: 50 μg of Spiroplasma sp. strain MQ1 DNA was partially digested with Sau 3A, using 0.16–0.3 units of enzyme/μg DNA and incubated for 20 minutes at 37° C. The reaction was stopped by heating to 65° C. for 15 minutes. The resulting fragments were separated on 10–40% sucrose gradients run for 23 hours at 22K rpm.

Fragments of 3–10 Kb average size were pooled and used for ligation.

3 Ligation and Transformation. The pooled fragments were ligated into a BamHI site of 50 μg dephosphorylated pUC 18 vector at a molar ratio of 3:1 (insert: vector DNA). The ligation reaction was carried out for 4 hours at 16° C. in standard ligation buffer: (60 mM Tris HCl pH 7.6, 1 mM ATP, 10 mM MgCl$_2$, 1 mM Spermidine, 15 mM DTT, 1 mg/ml BSA) supplemented with 300 units of T4 DNA ligase. Transformations were carried out in *E. coli* PR101/pSU77 according to Hanahan, D. (in DNA cloning Vol. 1, ed Glover, D. M. JRL Press Oxford pp 109–135, 1986).

4. Cell Library. The transformed culture was gently centrifuged, the supernatant was discarded and the cells were resuspended in 1 ml L-broth. 200 μl portions of the suspended cells were plated onto Luria-agar plates containing 50 μg/ml ampicillin. The plates were incubated overnight at 37° C. The transformed cells that grew up on the surfaces of the plates were collected by flooding each of the plates with L-broth and scraping the agar with a rubber policeman. An equal volume of 80% glycerol in L-broth was added and cell library was stored at −20° C. until use.

5. Plasmid Library. The cell library was amplified by inoculating 200 μl of the above suspension into 250 ml L-broth containing ampicillin (50 μg/ml) and incubated for 18 hours at 37° C. The cells were harvested by centrifugation at 4 krpm for 10 minutes. The pellet was resuspended in 6 ml of 25 mM Tris HCl pH 8.0, 10 mM EDTA, 15% sucrose. Lysozyme (16 mg) was added and the mix incubated on ice for 10 minutes. Freshly prepared 0.2N NaOH, 1% SDS were added and incubated for 10 minutes on ice. 7.5 ml of 3M sodium acetate, pH 4.6 was added and incubated on ice for additional 20 minutes. The lysate was spun at 30,000 xg for 15 minutes at 4° C. to remove chromosomal DNA and cell debris. To the clear supernatant 25μl RNase A (10 mg/ml) were added and DNA purified by phenol/chloroform/isoamyl alcohol (25:24:1) extractions followed by ethanol precipitation. The DNA was dissolved in 6–8 ml of water and purified on cesium chloride/ethidium bromide gradients as described (Maniatis et al. Molecular Cloning Cold Spring Harbor Laboratory, Cold Spring Harbor, N.Y. pp 93–94, 1982).

6. Digestion of the Plasmid Library. An aliquot of the plasmid library was transformed into *E. coli* PR101 harboring the opal suppressor in pSU77. The plates were flooded with L-broth and 40,000 colonies were collected with a rubber policeman. A 200 μl aliquot was inoculated into 250 ml of L-broth containing 50 μg/ml ampicillin and 17 μg/ml chloramphenicol and incubated at 37° C. As the cells reached a density of $10^8$ cell/ml, IPTG was added to a final concentration of 2.5 mM. The culture was propagated to reach confluency, the cells were harvested and plasmid prepared as in 5. Of the plasmid library 10 μg was digested to completion with 25 units of Hha I restriction endonuclease.

7. Transformation. The digested library was used to transform *E. coli* PR101 containing the opal suppressor in pSU77 as described in 3. The transformed culture was plated onto L-agar containing 50 μg/ml ampicillin and 17 μg/ml chloramphenicol. HhaI digestion reduced the number of transformants $10^5$ fold compared to transformation with undigested plasmid, sixty-five colonies were picked from the survivors of the HhaI digestion: each was inoculated into 2 ml of L-broth containing ampicillin and chloramphenicol. IPTG was added when the cultures reached $10^8$ cells/ml. Minicultures were propagated to confluency for miniplasmid preparations and streaked onto an L-agar plate to prepare a master stock.

8. Analysis of Surviving Individuals: Mini-preparation of plasmid DNA: The cells were pelleted in the microfuge for 1 minute and resuspended in 100 μl STET (8% sucrose, 5% triton X-100, 50 mM EDTA, 50 mM Tris pH 8.0). To this suspension 10 μl lysozyme (5 mg/ml) was added and the suspension incubated for 10 minutes at room temperature. The tubes were then placed in a boiling water bath for two minutes, transferred to ice water, and spun in a microfuge for 15 minutes. The pellet was removed with a sterile toothpick and discarded, and 110 μl of isopropanol added, mixed, and spun in a microfuge for 15 minutes. After the supernatant was removed, the pellets were vacuum dried and resuspended in 100 μl sterile water containing 50 μg/ml treated RNase A, and incubated for 30 minutes at 37° C. 3M sodium acetate pH 4.8, 1/10 volume, was added and the solution was extracted once with an equal volume of phenol/chloroform/isoamyl alcohol (25:24:1). The DNA was precipitated by the addition of two volumes of ethanol, mixed, placed at −20° C. for 20 minutes and spun for 15 minutes. The pellets were rinsed with 1 ml of 70% ethanol, spun for another 3 minutes, vacuum dried and resuspended in 25 μl sterile water. 2.5 μl was used for restriction enzyme digestion. The plasmid minipreps were subsequently analyzed by digestion with Hpa II and Msp I. Plasmids from clones 1, 5, 7, and 8, in FIG. 3 demonstrate resistance to cleavage by HpaII while sensitivity to cleavage by MspI. Plasmids from clones 2, 3, 4, and 6 demonstrated sensitivity to both HpaII and MspI cleavage. Therefore, clones 1, 5, 7, and 8 are likely candidates which encode an active CpG methylase.

Figure 4:
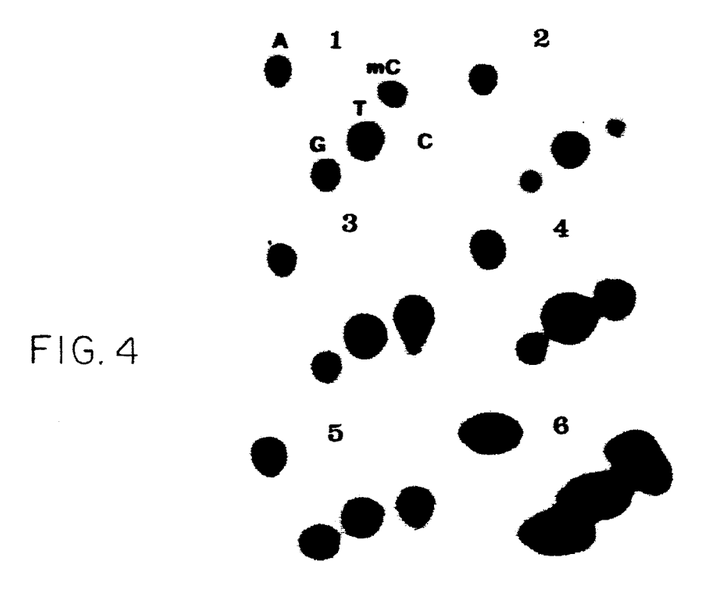
FIG. 4 illustrates the extent of methylation of plasmid DNA and chromosomal DNA at CpG sequences by nearest neighbor analysis. The sequence specificity of the enzyme in vivo is also demonstrated with plasmid DNA.

9. Spiroplasma sp. Strain MQ1 Methylase Gene Clones: Approximately half of the 65 plasmid DNA preparations that were analyzed were found to be sensitive to Msp I digestion and resistant to Hpa II (FIG. 3). Clones which were protected from digestion by the methyl sensitive (m5CpG) enzymes were analyzed by nearest neighbor analysis which showed >95% methylation of CpG sequences, while unprotected clones showed no 5 mC (FIG. 4). The nearest neighbor analysis also showed that only CpG sequences are methylated.

Nearest neighbor analysis: (FIG. 4) DNA was extracted from an overnight IPTG induced culture of a clone which harbored a plasmid which was resistant to cleavage by Hpa II. Chromosomal and plasmid DNA was seperated by CsCl ethidium bromide isopycnic centrifugation. DNA (1 µg) was randomly nicked with 1 ng DNAase I for 15 minutes at 37° C. and end labelled at the nicks with 200 µCi [α32P] labeled deoxynucleotide triphosphate (either dGTP, dATP, dTTP, or dCTP) and 40 units E. coli DNA polymerase I incubating for 30 minutes at 15° C. After purification of the labelled DNA on sephadex G-50 the DNA was digested to mononucleotides by micrococcal nuclease and spleen phosphodiesterase. The resulting 3' dNMPs were separated by 2-dimensional thin layer chromatography and autoradiographed. The relative radioactivity in 5-methyl dCMP and dCMP was determined by densitometry as described in Gruenbaum, Y., Stein, R., Cedar, H., and Razin, A., FEBS letters, 142, 67, 1981, the disclosure of which is hereby incorporated by reference. As depicted in FIG. 4, panels 1 thru 4, only when the nearest neighbor analysis was performed with dGTP as the source of radioactive label, was a radioactive spot indicating the presence of 5-methylcytosine detected. Furthermore there was no detectable spot for cytosine, indicating that all cytosines 5' of guanines were methylated. Whereas no 5-methylcytosine was 5' of any of the other three nucleotides. When nearest neighbor analysis was performed with dATP, dCTP, or TTP only spots for radioactive cytosine were detected. As shown in FIG. 4, panels 5 and 6 5-methylcytosine 5' of guanines was only detected in chromosomal DNA isolated from transformed E. coli cells, not from untransformed cells.

10. Subcloning the M.Sss MQ1 methylase gene. A DNA fragment from a clone which harbored a plasmid which was resistant to cleavage by Hpa II (Step 9), which was digested with Bgl II and Pst I, was inserted into a BamH I and Pst I cleaved Bluescript KS Minus (Stratagene Inc., LaJolla, Calif.) vector and transformed into E.coli PR101/pSU77. This resulted in a clone, E. coli PR101/pSU77/pMT100 which contained an active M.Sss MQ1 methylase encoded on a 1538 bp Bgl II DNA fragment and a DNA fragment containing the gene encoding the tRNA UGA suppressor, a sample of which has been deposited at the American Type Culture Collection under ATCC #68095 designation. FIG. 5 lists the DNA sequence of the 1538 base pair BglII DNA fragment. It is believed that the gene encoding the M.Sss MQ1 starts as position 103 and ends at position 1261. Also it should be noted that the UGA codons correspond to positions 229, 349, 595, and 709.

Figure 6:
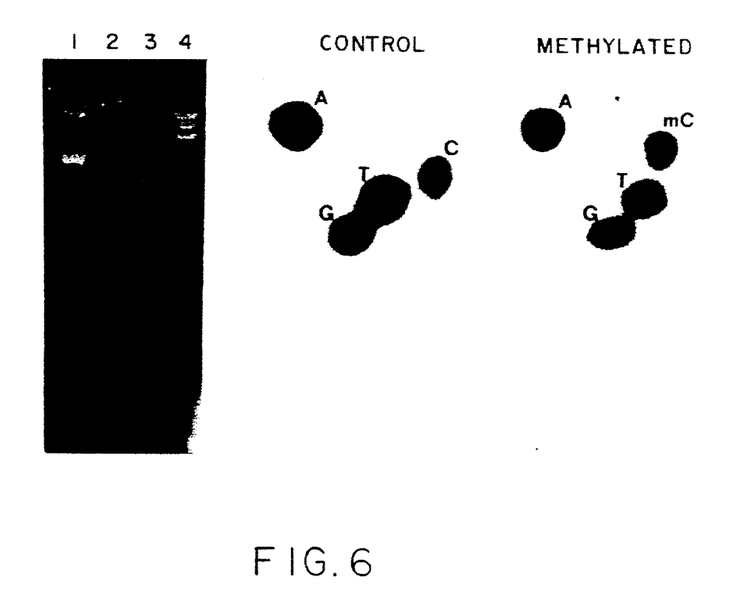
FIG. 6 demonstrates the activity and substrate specificity of the cloned methylase in cell free extracts.

11. Substrate and sequence specificity of the methylase in vitro: Crude extracts of E. coli PR101/pMT100/pSU77 were used to methylate φχ174 DNA in vitro. 2µg of φχ174 RF DNA was incubated in 50 µl volume containing 50 mM Tris HCl pH 8.0, 10 mM EDTA, 5 mM dithiothreitol, 1 mM S-adenosyl methionine, and crude extract for 18 hours at 28° C. The DNA was chloroform/phenol extracted. The resulting DNA was analyzed by two methods, the resistance to cleavage by HpaII restriction endonuclease (FIG. 6 lanes 1–4) and nearest neighbor analysis (FIG. 6 panels, control and methylated). φχ74 RF DNA that was incubated with the methylase preparation was resistant to cleavage by HpaII (lane 2) while the DNA that was not incubated with methylase preparation was cleaved by HpaII (lane 3). Lane 1 is undigested control and lane 4 is a molecular weight marker of lambda DNA digested with HindIII. The nearest neighbor analysis with [α32P] labeled dGTP demonstrated complete methylation at CpG sequences.

12. Preparation and Assay of Methylase: A culture of E. coli PR101/pMT100/pSU77 cells was grown to $5 \times 10^8$ cells/ml IPTG was added, and incubated overnight at 37° C. in L-broth containing 50 µg/ml ampicillin and 17 µg/ml chloramphenicol. The subsequent steps in the preparation of the methylase are carried out at 4° C. The culture was centrifuged at 4k rpm for 10 minutes and the cell pellet was ground with twice its wet weight of alumina 305. The paste was suspended in 5 vol. of buffer A (10% glycerol (Vol/Vol) 1 mM dithiothreitol, 1 mM EDTA, 40 mM Tris HCl pH 8.0). The homogenous suspension was centrifuged at 12,000 xg for 10 minutes. To the supernatant, 0.2 vol. of 20% (wt./vol.) streptomycin sulfate was slowly added with continuous stirring over a period of 30 minutes. The supernatant fluid was collected after 10 minutes centrifugation at $12,000 \times g$ and solid ammonium sulfate was added to 70% saturation, with continuous stirring over a period of 30 minutes. The pellet obtained after 10 minute centrifugation at $12,000 \times g$ was dissolved in buffer A and desalted on a sephadex G-50 column equilibrated with buffer A. The methylase activity was assayed in a reaction mixture (50 µl) containing 50 mM Tris HCl pH 8.0, 10 mM EDTA, 5 mM dithiothreitol, 1 mM S-adenosyl methionine [H3 methyl], 1–6 µg DNA and methylase preparations as described above (60 µg of protein). Reactions were incubated at 30° C. for 20 minutes. Reactions were terminated by the addition of 0.2 ml 1N NaOH, 1% SDS and 2 hours incubation at 60° C. DNA was extracted with 1 vol. chloroform: isoamyl alcohol (24:1). To an aliquot of the aqueous phase 50 µg calf thymus DNA was added and DNA precipated with cold 10% TCA collected and washed with 5% TCA on GF/C filters. Dried filters were subjected to liquid scintillation counting.

What is claimed is:

1. An isolated DNA sequence encoding a M.Sss MQ1 methylase of Spiroplasma, said DNA encoding the amino acid sequence set forth in FIG. 5.

2. A vector containing the DNA sequence of claim 1.

3. The vector of claim 2, further comprising the opal suppressor trp T146.

4. A microbial host transformed by the vector of claim 2, containing the DNA sequence for M.Sss MQI methylase.

5. The DNA of claim 1, wherein the DNA sequence comprises the sequence as shown in FIG. 5.

* * * * *